United States Patent [19]
Guskey et al.

[11] Patent Number: 5,840,288
[45] Date of Patent: Nov. 24, 1998

[54] ANTIPERSPIRANT GEL-SOLID STICK COMPOSITION CONTAINING A MODIFIED SILICONE CARRIER

[75] Inventors: Gerald John Guskey, Montgomery; Thomas Vincent Orr, Cincinnati; James Robert Schwartz, West Chester, all of Ohio; James Merle Heinrich, Fairfield, Conn.

[73] Assignee: Procter & Gamble Company, Cincinnati, Ohio

[21] Appl. No.: 771,614

[22] Filed: Dec. 20, 1996

[51] Int. Cl.⁶ .............................. A61K 7/32; A61K 7/34; A61K 7/38; A61K 7/00
[52] U.S. Cl. .............................. 424/65; 424/66; 424/68; 424/400; 424/401; 424/DIG. 5
[58] Field of Search .................. 424/65, 66, 68, 424/401, 400, DIG. 5

[56] References Cited

U.S. PATENT DOCUMENTS

| | | | |
|---|---|---|---|
| 2,890,987 | 6/1959 | Hilfer | 167/90 |
| 2,900,306 | 8/1959 | Slater | 167/90 |
| 3,255,082 | 6/1966 | Barton | 167/90 |
| 3,792,068 | 2/1974 | Luedders | 260/429.3 |
| 3,887,692 | 6/1975 | Gilman | 423/462 |
| 3,903,258 | 9/1975 | Siegal | 424/66 |
| 3,904,741 | 9/1975 | Jones et al. | 423/462 |
| 3,969,087 | 7/1976 | Saito et al. | 44/7 C |
| 3,970,748 | 7/1976 | Mecca | 424/68 |
| 3,979,510 | 9/1976 | Rubino | 424/47 |
| 3,981,896 | 9/1976 | Pauling | 260/429 |
| 4,017,599 | 4/1977 | Rubino | 424/47 |
| 4,049,792 | 9/1977 | Elsnau | 424/66 |
| 4,053,581 | 10/1977 | Pader et al. | 424/68 |
| 4,126,679 | 11/1978 | Davy et al. | 424/66 |
| 4,137,306 | 1/1979 | Rubino | 424/68 |
| 4,147,766 | 4/1979 | Kozischek | 424/14 |
| 4,151,272 | 4/1979 | Geary | 424/68 |
| 4,154,816 | 5/1979 | Roehl et al. | 424/68 |
| 4,202,879 | 5/1980 | Shelton | 424/66 |
| 4,226,889 | 10/1980 | Yuhas | 424/66 |
| 4,331,609 | 5/1982 | Orr | 424/68 |
| 4,371,645 | 2/1983 | Mahaffey, Jr. | 524/108 |
| 4,425,328 | 1/1984 | Nabial | 424/68 |
| 4,429,140 | 1/1984 | Murial et al. | 549/370 |
| 4,518,582 | 5/1985 | Schamper et al. | 424/66 |
| 4,639,369 | 1/1987 | Ciaudelli | 424/59 |
| 4,719,102 | 1/1988 | Randhawa et al. | 424/66 |
| 4,722,835 | 2/1988 | Schamper et al. | 424/66 |
| 4,725,430 | 2/1988 | Schamper et al. | 424/66 |
| 4,725,432 | 2/1988 | May | 424/66 |
| 4,743,444 | 5/1988 | McCall | 424/66 |
| 4,781,917 | 11/1988 | Luebbe et al. | 424/65 |
| 4,816,261 | 3/1989 | Luebbe et al. | 424/65 |
| 4,822,602 | 4/1989 | Sabatelli | 424/65 |
| 4,822,603 | 4/1989 | Farris et al. | 424/66 |
| 4,840,789 | 6/1989 | Orr et al. | 424/65 |
| 4,853,214 | 8/1989 | Orr | 424/69 |
| 4,919,934 | 4/1990 | Deckner et al. | 424/402 |
| 4,944,937 | 7/1990 | McCall | 424/65 |
| 4,944,938 | 7/1990 | Potini | 424/68 |
| 4,948,578 | 8/1990 | Burger et al. | 424/68 |
| 4,980,156 | 12/1990 | Raleigh et al. | 424/66 |
| 4,985,238 | 1/1991 | Tanner et al. | 424/66 |
| 4,987,243 | 1/1991 | Kawam et al. | 556/27 |
| 5,019,375 | 5/1991 | Tanner et al. | 424/66 |
| 5,023,354 | 6/1991 | Salome et al. | 549/364 |
| 5,102,656 | 4/1992 | Kasat | 424/66 |
| 5,106,999 | 4/1992 | Gardlik et al. | 549/364 |
| 5,156,834 | 10/1992 | Beckmeyer et al. | 424/47 |
| 5,169,626 | 12/1992 | Tanner et al. | 424/66 |
| 5,200,174 | 4/1993 | Gardlik et al. | 424/66 |
| 5,232,689 | 8/1993 | Katsoulis et al. | 424/66 |
| 5,346,694 | 9/1994 | Juneja | 424/66 |
| 5,384,117 | 1/1995 | Vu et al. | 424/66 |
| 5,429,816 | 7/1995 | Hofrichter et al. | 424/66 |
| 5,449,511 | 9/1995 | Coe | 424/66 |
| 5,455,026 | 10/1995 | Bahr et al. | 424/65 |
| 5,480,637 | 1/1996 | Smith | 424/78.02 |
| 5,486,566 | 1/1996 | Katsoulis | 524/773 |
| 5,492,691 | 2/1996 | Bahr et al. | 404/65 |
| 5,500,209 | 3/1996 | Ross et al. | 424/66 |
| 5,531,986 | 7/1996 | Shevade et al. | 424/68 |
| 5,552,136 | 9/1996 | Motley | 424/68 |

FOREIGN PATENT DOCUMENTS

| | | | |
|---|---|---|---|
| 1266003 | 4/1986 | Canada | A61K 7/32 |
| 2054478 | 5/1992 | Canada | A61K 007/32 |
| 0 295 070 | 12/1988 | European Pat. Off. | A61K 7/32 |
| 0 295 071 | 12/1988 | European Pat. Off. | A61K 7/32 |
| 0 396 137 | 11/1990 | European Pat. Off. | A61K 7/32 |
| 0 448 278 | 9/1991 | European Pat. Off. | A61K 7/38 |
| 530866 A1 | 3/1993 | European Pat. Off. | A61K 7/48 |
| 0 616 842 A1 | 9/1994 | European Pat. Off. | B01J 13/00 |
| 0 682 940 A1 | 11/1995 | European Pat. Off. | A61K 7/48 |
| A61 206 450 | 9/1986 | Japan | A61L 9/01 |
| A62 265393 | 11/1987 | Japan | C10L 3/00 |
| A10 20286 | 1/1989 | Japan | C09K 9/01 |
| 64-62377 | 3/1989 | Japan . | |
| 1-207223 | 8/1989 | Japan | A61K 7/02 |
| 2-180805 | 7/1990 | Japan | A61K 7/00 |
| 2-264707 | 10/1990 | Japan . | |
| 3-170415 | 7/1991 | Japan | A61K 7/32 |
| A 42 08 202 | 7/1992 | Japan | A01N 25/18 |
| 1485694 | 9/1977 | United Kingdom | B01F 17/28 |
| 2253347 | 9/1992 | United Kingdom | A61K 7/32 |
| 2299024 | 9/1996 | United Kingdom | A61K 7/32 |
| WO 96/26709 | 9/1996 | WIPO | A61K 7/32 |

OTHER PUBLICATIONS

M. F. Bobin, C. Suzza and M–C. Martini, "Using Fluorinated Compounds in Topical Preparations", 111 *Cosmetics and Toiletries* 47–63, Oct. 1996.

Taro Tachibana and Hideko Kambara, "Studies of Helical Aggregates of Molecules. I. Enantiomorphism in the Helical Aggregates of Optically Active 12–Hydroxystearic Acid and Its Lithium Salt", *Bulletin of the Chemical Society of Japan*, vol. 42, 3422–3424 (1969).

Taro Tachibana, Shyoko Kitazawa and Hideko Takeno, "Studies of Helical Aggregates of Molecules. II, The Sense of Twist in the Fibrous Aggregates from the Alkali Metal Soaps of Optically Active 12–Hydroxystearic Acid", *Bulletin of the Chemical Society of Japan*, vol. 43 2418–2421 (1970).

"Electron Microscopic and Thermal Studies of Optically Active 12–Hydroxystearic Acids in Soap Formation", *Journal of Colloid and Interface Science*, vol. 51, No. 2, May 1975.

"Morphology of Collapsed Monolayers of Optically Active and Racemic 12–Hydroxystearic Acids", *Journal of Colloid and Interface Science*, vol. 61, No. 2, Sep. 1977.
Balsam and Sagarin, Cosmetics, Science, and Technology, vol. 1, 27–104, 1972.
Geria, "Formulation of Stick Antiperspirants and Deodorants", *Cosmetics and Toiletries*, 99:55–60 (1984).
Gels and Sticks Formulary, 99 *Cosmetics and Toiletries* 82–87, 1984.
Todd et al., "Volatile Silicone Fluids for Cosmetics", *Cosmetics and Toiletries*, 91:29–32 (1976).
Chemical Abstracts, vol. 85, No. 2, Jul. 12, 1976 No. 85:10310.
Taro Tachibana, Tomoko Mori and Kayako Hori, "New type of twisted mesophase in jellies and solid films of chiral 12–hydroxyoctadecanoic acid", *Nature*, vol. 278, Apr. 1979.
Tachibana, Mori and Hori, "Chiral Mesophases of 12–Hydroxyoctadecanoic Acid in Jelly and in the solid State. II. A new Type of Mesomorphic Solid State", *Bulletin of the Chemical Society of Japan*, vol. 54, 73–80 (1981).
C. D. Vaughn, "Solubility Effects in Product, Package, Penetration and Preservation" 103 *Cosmetics and Toiletries* 47–69, Oct. 1988.
Plechner, *Antiperspirants and Deodorants*, 2 Cosmetics, Science and Technology, Balsam and Sagarin, 374–400, 1972.
Homma, Masao, Oil Gelating Agent Utilizing Amino Acids, (Modern Chemistry), 54–59, Aug. 1987 (Translation).
C. D. Vaughn, "Using Solubility Parameters in Cosmetics Formulation", 36 *J. Soc. Cosmetic Chemists* 319–333 Sep./Oct., 1985.
Tsau, Heller and Pratap, "Thermoreversible Organogels of 12–Hydroxystearic Acid", *Polymer Preprints* 1994 35, 737–738.

*Primary Examiner*—Shelley A. Dodson
*Attorney, Agent, or Firm*—William J. Winter; David L. Suter; Tara M. Rosnell

[57] ABSTRACT

Disclosed are anhydrous antiperspirant gel-solid sticks which comprise particulate antiperspirant active; a solid non-polymeric gellant that is substantially free of dibenzylidene alditol, inorganic thickening agents, organic polymeric gellants, n-acyl amino acid derivatives, or combinations thereof; an anhydrous liquid carrier containing polyalkylsiloxanes, polyalkyarylsiloxanes, polyestersiloxanes, polyethersiloxane copolymers, polyfluorosiloxanes, polyaminosiloxanes, or combinations thereof. The composition has a visible residue index of from about 11 to about 30 L-value, a product hardness of from about 500 to about 5,000 gram·force, a rheology profile defined by a ratio of an elastic modulus (G') to a viscous modulus (G") of from about 0.1 to about 100. The refractive indices of the particulate antiperspirant active, the solid non-polymeric gellant, and the anhydrous liquid carrier are not matched. The compositions preferably comprise crystalline gellant particles having an average particle size of less than about 1 $\mu$m and/or a particle morphology having an aspect ratio of greater than about 2. These compositions provide improved low residue performance, efficacy and aesthetics.

25 Claims, No Drawings

ANTIPERSPIRANT GEL-SOLID STICK COMPOSITION CONTAINING A MODIFIED SILICONE CARRIER

TECHNICAL FIELD

The present invention relates to antiperspirant compositions in the form of gel-solid sticks. In particular, the present invention relates to select compositions in the form of gel-solid sticks that provide improved low residue performance, efficacy and aesthetics, and which contain select modified silicone carriers.

BACKGROUND OF THE INVENTION

There are many types of topical antiperspirant products that are commercially available or otherwise known in the antiperspirant art. Most of these products are formulated as aerosol or pump sprays, roll-on liquids, creams, emulsions, gels, gel-solids, or other solid stick formulations, and comprise an astringent material, e.g. zirconium or aluminum salts or combinations thereof, incorporated into a suitable carrier. These products are designed to provide effective perspiration and odor control while also being cosmetically acceptable during and after application onto the axillary area or other areas of the skin.

Within this product group, solid antiperspirant sticks have become especially popular among consumers. These antiperspirant sticks comprise a solid matrix within which the antiperspirant active material is contained. The active can be solubilized in a liquid carrier comprising water, glycols and/or other alcohols, or maintained within a solid matrix as dispersed solids in an anhydrous system. The solid sticks which contain dissolved active often provide some low residue performance, but tend to be wet or sticky during and immediately after application to the skin, and more importantly, are often not as effective in providing antiperspirant and deodorant performance as solid sticks containing dispersed particulate active. Although the antiperspirant sticks which contain particulate actives are more effective, they also tend to leave a higher visible residue on the skin.

There have been many attempts at producing anhydrous antiperspirant sticks which contain dispersed particulate antiperspirant active, and which also provide improved efficacy and low residue performance during and after application to the skin, or which otherwise provide product clarity prior to (as a packaged product) or after such application (as a clear or low-residue film on the skin).

One such attempt involves the combination of particulate antiperspirant active, gellants and liquid carrier in a gel stick, wherein all such components in the combination have matching refractive indices. Refractive index matching allows for more passage of light through the gel stick with less scattering of the light, thus resulting in products which appear more clear or translucent as a packaged composition or when initially applied topically to the skin. These gel sticks, however, are expensive to make due to the cost of using raw materials having only select matching refractive indices. These compositions are also very difficult to formulate given that refractive index matching for a three component system (particulate active, solvent and gellant) is extremely difficult, and greatly limits the materials that can be used to prepare such a formulation.

Another attempt at making low residue antiperspirant sticks involves the use of gellants such as dibenzylidene alditols. These gellants, however, like many other gellants known in the art, are not acid stable and therefore tend to interact with the antiperspirant active due to the acidic nature of the active. This interaction can result in reduced efficacy of the active, poor gel formation, and lower gel stability over extended periods during shipping or storage. This interaction may also cause processing difficulties at the temperatures and holding times often used during the formulation and manufacturing process. These gellants are also commonly used in combination with glycol carriers or other solvents which tend to be wet and sticky and irritating to the skin.

Yet another attempt at making low residue antiperspirant sticks involves the use of residue masking agents such as non-volatile paraffinic hydrocarbon fluids, phenyl trimethicone, low melting point waxes and combinations thereof. These agents are used in combination with stearyl alcohol or other high residue waxes commonly used in solid antiperspirant sticks. These agents help reduce visible residue during and immediately after application of the solid stick to the skin, but also tend to be associated with an oily or sticky skin feeling during application. Moreover, although the visible residue is reduced in such compositions, there remains a visible residue on the skin when used in combination with high residue waxes such as stearyl alcohol, and this reduced residue is still more visible or apparent than the topical residue left by antiperspirant sticks which contain solubilized antiperspirant active.

Other attempts at improving low residue performance from an antiperspirant composition has focused on the use of anhydrous antiperspirant creams. These creams can be applied to the skin by conventional means, or by a cream applicator device, and results in very low residue during and immediately after application to the skin. These compositions comprise particulate active dispersed throughout an anhydrous carrier, and either contained within a solid-like matrix or thickened with an inorganic or polymeric gellant or thickening agent. Many consumers, however, still prefer the convenience of using a solid antiperspirant stick, even if the solid stick tends to leave a higher visible residue on the skin.

A recent method of making low residue antiperspirant sticks is described in U.S. Pat. No. 5,429,816, issued to Hofrichter et al. on Jul. 4, 1995, which description is hereby incorporated by reference herein. The antiperspirant sticks provide low visible residue during and immediately after application to the skin, and are physically and chemically stable over extended periods of time. The improved antiperspirant sticks comprise a dual gellant system having a primary gellant such as 12-hydroxystearic acid or esters or amides thereof and a secondary gellant such as n-acyl amino acid derivatives. Formation of such an antiperspirant stick with such a dual gellant system has been characterized as a "gel-solid" antiperspirant stick.

An antiperspirant gel-solid, such as that described by Hofrichter et. al., is an antiperspirant stick having a three-dimensional, non-polymeric, gel network in which solvent is contained or trapped. These gel-solids are typically formed by solubilizing the gellant in the solvent at temperatures above the melt point of the gellant and at temperatures at which the melted gellant is soluble in the solvent, and then cooling the composition to form the desired gel-solid composition. The low residue gel-solids described by Hofrichter et al. are remarkably stable, both physically and chemically, and will maintain the desired product hardness over an extended period of time. The gel-solids described by Hofrichter et al., however, are limited to select dual gellant systems and do not include or otherwise describe any method of making a low-residue antiperspirant gel-solid stick containing any other gellant or gellant system.

It has now been found that other low-residue gel-solids can be formulated without reliance upon the select combination of gellants described by Hofrichter et al. The new low-residue gel-solids are anhydrous systems which comprise from about 0.5% to about 60% by weight of particulate antiperspirant active; from about 1% to about 15% by weight of a solid non-polymeric gellant that is substantially free of dibenzylidene alditol, inorganic thickening agents, organic polymeric thickening agents, n-acyl amino acid derivatives and combinations thereof; from about 10% to about 80% by weight of an anhydrous liquid carrier containing a modified silicone liquid carrier selected from the group consisting of polyalkylsiloxanes, polyalkyarylsiloxanes, polyestersiloxanes, polyethersiloxane copolymers, polyfluorosiloxanes, polyaminosiloxanes, and combinations thereof; wherein the composition has a visible residue index of from about 11 to about 30 L-value, a product hardness of from about 500 gram-force to about 5,000 gram-force, a ratio of an elastic modulus (G') to a viscous modulus (G") of from about 0.1 to about 100. The composition does not require refractive index matching of the particulate antiperspirant active, solid non-polymeric gellant, and anhydrous liquid carrier to achieve low residue performance. The compositions preferably comprise gellant crystalline particles having an average particle size of less than about 1 μm, and/or an elongated particle morphology defined by an aspect ratio of greater than about 2.

It also has been found that the modified silicone carriers, when incorporated into the antiperspirant gel-solid stick compositions as defined herein, are effective in providing improved antiperspirant and deodorant efficacy. These select modified silicone carriers are especially effective when used in combination with other carrier liquids such as volatile silicones, and even more effective when used as a co-solvent for the solid non-polymeric gellant in place of other more typical or conventional co-solvents such as polar, water-immiscible, co-solvents.

It is therefore an object of the present invention to provide an anhydrous antiperspirant gel-solid stick containing particulate antiperspirant active which provides improved low residue performance, efficacy and aesthetics, and further to provide such a composition without reliance upon specific gellants such as dibenzylidene alditols, or dual gellant systems containing n-acyl amino acid derivatives. It is a further object of the present invention to provide such a composition without reliance upon refractive index matching of component materials, or the use of solubilized antiperspirant active, to obtain product clarity or low residue performance. It is yet another object of the present invention to provide such a composition comprising an anhydrous liquid carrier containing select modified silicone carriers.

SUMMARY OF THE INVENTION

The present invention is directed to anhydrous antiperspirant gel-solid stick compositions which comprise from about 0.5% to about 60% by weight of particulate antiperspirant active; from about 1% to about 15% by weight of a solid non-polymeric gellant that is substantially free of dibenzylidene alditol, inorganic thickening agents, organic polymeric gellants, n-acyl amino acid derivatives, or combinations thereof; from about 10% to about 80% by weight of an anhydrous liquid carrier containing a modified silicone liquid carrier selected from the group consisting of polyalkylsiloxanes, polyalkyarylsiloxanes, polyestersiloxanes, polyethersiloxane copolymers, polyfluorosiloxanes, polyaminosiloxanes, and combinations thereof; and wherein the composition has a visible residue index of from about 11 to about 30 L-value, a product hardness of from about 500 gram-force to about 5,000 gram-force, a rheology profile defined by a ratio of an elastic modulus (G') to a viscous modulus (G") of from about 0.1 to about 100. The refractive indices of the particulate antiperspirant active, the solid non-polymeric gellant, and the anhydrous liquid carrier are not matched. The compositions preferably comprise crystalline gellant particles having an average particle size of less than about 1 μm and/or a particle morphology having an aspect ratio of greater than about 2. The compositions also preferably comprise from about 0.1% to about 50% by weight of the modified silicone liquid carrier, and more preferably in combination with a volatile silicone.

It has been found that the antiperspirant gel-solid stick compositions of the present invention can provide low residue performance without the need to use solubilized antiperspirant active, and without reliance upon select low residue gellants such as dibenzylidene alditols or select gellant combinations containing n-acyl amino acid derivatives. This is accomplished by formulating an anhydrous gel-solid stick composition having the select hardness and rheology profile preferably provided by a non-polymeric, three-dimensional crystalline gel network made up of small, elongated crystalline particles having an average particle size of less than about 1 μm and/or a particle morphology defined by an aspect ratio of at least about 2.

It also has been found that the modified silicone carriers, when incorporated into the antiperspirant gel-solid stick compositions as defined herein, are effective in providing improved antiperspirant and deodorant efficacy. These select modified silicone carriers are especially effective when used in combination with other carrier liquids such as volatile silicones, and even more effective when used as a co-solvent for the solid non-polymeric gellant in place of other more typical or conventional co-solvents such as polar, water-immiscible, co-solvents.

DETAILED DESCRIPTION OF THE INVENTION

The antiperspirant gel-solid stick compositions of the present invention are anhydrous systems which are dispersions of particulate antiperspirant active held or contained within a non-polymeric crystalline gel-solid matrix.

The term "anhydrous" as used herein means that the antiperspirant gel-solid stick composition of the present invention, and the essential or optional components thereof other than the particulate antiperspirant active, are substantially free of added or free water. From a formulation standpoint, this means that the antiperspirant gel-solid stick compositions of the present invention preferably contain less than about 5%, preferably less than about 3%, more preferably less than about 1%, most preferably zero percent, by weight of free or added water, other than the water of hydration typically associated with the particulate antiperspirant active prior to formulation.

The term "low residue" as used herein refers generally to the visible residue left on the applied areas of the skin during or immediately after application, and more specifically refers to the visible residue index of the composition as defined by the methodology described hereinafter.

The term "ambient conditions" as used herein refers to surrounding conditions under about one atmosphere of pressure, at about 50% relative humidity, and at about 25° C., unless otherwise specified.

The term "substantially free" as used herein, unless otherwise specified, refers to preferred negative limitations of the compositions of the present invention, and are directed to the amount or concentration of inorganic thickening agents, organic polymeric thickening agents, dibenzylidene alditol gellants, n-acyl amino acid derivatives, or combinations thereof, in the composition. The term "substantially free" means that the compositions preferably contain less than an effective amount of such agents when used alone to provide any thickening or measurable viscosity increase to the composition. In this context, the negative limitations pertain only to those thickening or gelling agents which are also solid under ambient conditions, and which are not silicone containing materials or polymeric derivatives of 12-hydroxystearic acid. Generally, the compositions preferably contain less than 5%, preferably less than 2%, more preferably less than 1%, even more preferably less than 0.5%, most preferably zero percent, of such agents by weight of the composition. Examples of inorganic thickening agents to which the above-described negative limitations pertain include finely divided or colloidal silicas, fumed silicas, and silicates, which includes montmorillonite clays and hydrophobically treated montmorillonites, e.g., bentonites, hectorites and colloidal magnesium silicates. Examples of organic polymeric gelling agents to which the above-described negative limitations pertain include organic polymers well known in the antiperspirant or personal care art for use in providing gelling or thickening or other physical or aesthetic benefits to a composition, specific examples of which include hydrogenated butylene/ethylene/styrene copolymer, polyethylene, oxidized polyethylene, polyamides, acrylic acid polymers, ethylene acrylate copolymers, and other organic polymeric gelling agents described in Rheological Properties of Cosmetics and Toiletries, Edited by Dennis Laba, published by Marcel Dekker, In., New York (1993), which description is incorporated herein by reference.

The term "substituted" as used herein, unless otherwise specified, refers to chemical moieties or substituents known or otherwise suitable for attachment to the compounds or other chemical materials described or referred to herein. These substituents include, but are not limited to, those listed and described in C. Hansch and A. Leo, *Substituent Constants for Correlation Analysis in Chemistry and Biology* (1979), which listing and description are incorporated herein by reference. Examples of such substituents include, but are not limited to, alkyl, alkenyl, alkoxy, hydroxy, oxo, nitro, amino, aminoalkyl (e.g., aminomethyl, etc.), cyano, halo (e.g., chlorine, fluorine, bromine, iodine), carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, amides, esters, ethers, combinations thereof, and the like.

The term "n-acyl amino acid derivatives" refers to gellants selected from the group consisting of n-acyl amino acid amides, n-acyl amino acid esters prepared from glutamic acid, lysine, glutamine, apartic acid, and combinations thereof, and which are specifically disclosed in U.S. Pat. No. 5,429,816.

The terms "alkyl" and "alkenyl" as used herein, unless otherwise specified, refer to substituted or unsubstituted, branched, cyclic or linear, hydrocarbons having from 1 to about 22 carbon atoms.

The term "volatile" as used herein refers to materials which have a vapor pressure under ambient conditions of at least about 0.2 mm of Hg. Conversely, the term "non-volatile" as used herein refers to materials which have no measurable vapor pressure or which have a vapor of less than about 0.2 mm of Hg under ambient conditions.

The solid non-polymeric gellant, antiperspirant active and anhydrous liquid carrier components of the gel-solid stick compositions herein are preferably not refractive index matched, and more preferably have at least two of such components with refractive indices ($\eta_D$) that differ by at least about 0.02, more preferably by at least about 0.04.

The antiperspirant gel-solid stick compositions of the present invention can comprise, consist of, or consist essentially of the essential elements and limitations of the invention described herein, as well as any of the additional or optional ingredients, components, or limitations described herein.

As percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

Product Characteristics

The antiperspirant gel-solid stick compositions of the present invention are characterized in terms of product hardness, visible residue index, and a rheology profile defined by a ratio of an elastic to viscous moduli. Each of these characteristics is defined in accordance with the methodologies and other limitations described hereinafter.

a) Hardness

The antiperspirant gel-solid stick compositions of the present invention have a product hardness of from about 500 gram·force to about 5,000 gram·force, preferably from about 750 gram·force to about 2,000 gram·force, more preferably from about 800 gram·force to about 1,400 gram·force.

The term "product hardness" as used herein is a reflection of how much force is required to move a penetration cone a specified distance and at a controlled rate into an antiperspirant gel-solid stick composition under the following test conditions. Higher values represent harder product, and lower values represent softer product. These values are measured at 27° C., 15% relative humidity, using a TA-XT2 Texture Analyzer, available from Texture Technology Corp., Scarsdale, N.Y., U.S.A. The product hardness value as used herein represents the amount of force required to move a standard 45° angle penetration cone through the composition for a distance of 10 mm at a rate of 2 mm/second. The standard cone is available from Texture Technology Corp., as part number TA-15, and has a total cone length of about 24.7 mm, angled cone length of about 18.3 mm, a maximum diameter of the angled surface of the cone of about 15.5 mm. The cone is a smooth, stainless steel construction and weighs about 17.8 grams.

b) Residue

The antiperspirant gel-solid stick compositions of the present invention have a visible residue index of from 11 to about 30 L-value, preferably from about 11 to about 25 L-value, more preferably from 11 to about 20 L-value. The term "visible residue index" as used herein refers generally to the extent to which the composition of the present invention is visibly apparent as a thin topical film after application to the skin, and more specifically refers to visible residue values (expressed as an L-value on the L, a, b color scale) as measured in accordance with the following methodology, performed at 27° C., under atmospheric pressure, and at 15% relative humidity on antiperspirant stick compositions having a product hardness of from about 500 gram·force to about 5,000 gram·force.

A piece of black felt, approximately 10 cm×30 cm, is attached to a movable horizontal slide which is movably attached or fixed to a larger mechanical unit. An example of a suitable piece of black felt for use herein is Supreme Robe Velour, FN-6554, Color 404L, Style 31854, available from So-Fro Fabrics, Evendale, Ohio, U.S.A. An example of a suitable mechanical assembly for use herein is the Release and Adhesion Tester, Serial No. A-14934, manufactured by Testing Machines, Inc., Amityville, N.Y., U.S.A., or a Velmex Unislide Positioning System, Unislide assembly series (MB6000), available from Velmex, Inc., Bloomfield, N.Y., U.S.A. An antiperspirant stick composition contained within and partially extending out about 0.5 cm from a conventional package or container is positioned perpendicular to and above the attached piece of felt, such that the product extending out of the package or container is facing the piece of felt and the surrounding package is positioned away from the piece of felt. The surrounding package is positioned in place using a mechanical arm or other device suitable for applying the requisite movement to the product as described herein.

The antiperspirant stick composition is then slowly moved toward and allowed to gently contact the attached piece of black felt. A 1,000 gram weight is placed on the product sample so that the product continuously contacts the piece of black felt during testing. The weighted sample is then moved repeatedly back and forth across the piece of felt at a fixed speed (about 3 cm/second), and with a fixed amount of applied pressure provided by the weighted product, until the about 1.75 grams of the antiperspirant stick composition is evenly applied over a 5 cm×20 cm area of the piece of black felt. The piece of felt is then carefully removed from the apparatus.

A calibrated Minolta CR-300 chromameter (available from Minolta Corp., Ramsey, N.J., U.S.A.) is then used to measure the L-value (on the L,a,b color scale) of the applied surface area. First, a template is placed on top of the piece of felt to facilitate the Minolta readings. Template dimensions are 5 cm×20 cm. The template has twelve circular openings (2.2 cm diameter) positioned within the template, each opening positioned centrally within adjacent 6.5 $cm^2$ areas of the template surface. The template is positioned over the applied surface area of the piece of felt such that each of the twelve circular openings covers a non-overlapping area of the applied surface. The chromameter's view port is fitted into each of the circular openings and L-value measurements taken. An average L-value is then determined for the twelve measurements (standard deviation of less than about 0.8) which then corresponds to the visible residue index as described herein.

It has been found that there is a correlation between the visible residue index range defined herein and the average particle size of the crystalline gellant particles in the antiperspirant gel-solid stick composition of the present invention. Generally, as the average particle size of crystalline gellant particles in the composition decreases, low residue performance improves. In particular, it has been found that a visible residue index of from about 11 to about 30 L-value correlates with an average crystalline gellant particle size of less than about 1 μm, and/or a crystalline gellant particle morphology characterized by one dimensional crystalline growth such as that resulting in crystalline filaments, fibers, strings or other elongated particles, wherein the aspect ratio as defined by the major and minor axis of the crystalline particle is greater than about 2, preferably greater than about 6. Conversely, solid compositions containing crystalline gellant particles greater than 1 μm (average particle diameter) have a visible residue index of greater than 30 L-value. In view of this correlation between visible residue index values and average crystalline particle size or elongated particle morphology, the visible residue index measurement can now be used as an alternative means for establishing average crystalline gellant particle size or crystalline gellant morphology, at least to the extent that such average particle size is less than about 1 μm.

c) Rheology

The antiperspirant stick compositions of the present invention are gel-solids having the select rheology profile defined herein. This rheology profile is defined herein in terms of the elastic (G') to viscous (G") moduli ratio (G'/G") of the gel-solid stick composition. To provide the requisite rheology, the gel-solid stick compositions must have a G'/G" ratio of from about 0.1 to about 100, preferably from about 0.1 to about 50, more preferably from about 1 to about 20, even more preferably from about 5 to about 20. This ratio represents the extent to which the gel-solid stick compositions herein exhibit solid character and the extent to which the compositions exhibit liquid or fluid character, and specifically refers to the numerical ratio G'/G" as determined by the following methodology.

The elastic modulus is a measurement which correlates with the solid character of the gel-solid stick compositions herein, and the viscous modulus is a measurement which correlates with the fluid or liquid character of the gel-solid stick compositions herein. Measurements for G' and G" for purposes of defining the composition of the present invention are determined under ambient conditions using conventional techniques well known in the formulation arts. For example, a Bohlin Stress-Strain Rheometer, available from Bohlin Reologi, Cranberry, N.J., can be used using a cone (about 1°) and plate configuration. About 1.0 mg of the product is carefully removed for the composition with minimal application of shear force and is then placed between the cone and plate fixtures for measurement of G' and G".

It has been found that the gel-solid stick compositions of the present invention exhibit improved low residue performance when formulated as described herein, wherein the composition has the select G'/G" ratio described hereinabove, especially when the defined rheology is associated with a crystalline gel matrix having a preferred small particle size and/or particle morphology as described herein. These gel-solid stick formulations spread smoothly over the skin, and shear quickly and melt during such spreading to form a thin, low residue film over the applied surface.

In particular, it has been found that the gel-solid stick compositions of the present invention have rheology characteristics that result in improved performance, especially low residue performance. These select gel-solid compositions as defined herein behave as solids prior to application while maintained within a canister or other package, but behave more as liquids or fluids during or immediately after application to the skin. In other words, the solid compositions shear thin during application to the skin, melt or almost melt (except for particulate active which remains unmelted) during the shear thinning application, thus resulting in a thin, low residue, liquid or fluid film on the skin during or immediately after topical application to the skin. The applied film is clear or has very low visible residue, and remains substantially as such over extended periods of time after application.

Antiperspirant Active

The antiperspirant gel-solid stick compositions of the present invention comprise particulate antiperspirant active suitable for application to human skin. These particulate actives must remain substantially unsolubilized as dispersed or precipitated solids in the anhydrous or substantially anhydrous systems as described herein. The concentration of particulate active in the composition should be sufficient to provide the desired perspiration wetness and odor control from the antiperspirant gel-solid stick formulation selected.

The antiperspirant gel-solid stick compositions of the present invention preferably comprise particulate antiperspirant active at concentrations of from about 0.5% to about 60%, more preferably from about 5% to about 35%, by weight of the composition. These weight percentages are calculated on an anhydrous metal salt basis exclusive of water and any complexing agents such as glycine, glycine salts, or other complexing agents. The particulate antiperspirant active as formulated in the composition are in the form of dispersed solid particles having a preferred average particle size or diameter of less than about 100 μm, more preferably from about 15 μm to about 100 μm, even more preferably from about 20 μm to about 100 μm. Also preferred are dispersed solid particulates having an average particle size or diameter of less than about 2 μm, even more preferably from less than about 0.4 μm. It has been found that antiperspirant active particles within the preferred particle size ranges provide lower visible residue performance from the gel-solid compositions herein than other less preferred particle size ranges.

The antiperspirant active for use in the antiperspirant gel-solid stick compositions of the present invention include any compound, composition or other material having antiperspirant activity. Preferred antiperspirant actives include the astringent metallic salts, especially the inorganic and organic salts of aluminum, zirconium and zinc, as well as mixtures thereof. Particularly preferred are the aluminum and zirconium salts, such as aluminum halides, aluminum chlorohydrate, aluminum hydroxyhalides, zirconyl oxyhalides, zirconyl hydroxyhalides, and mixtures thereof.

Preferred aluminum salts for use in the antiperspirant gel-solid stick compositions include those which conform to the formula:

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorhydroxides referred to as "5/6 basic chlorhydroxide", wherein a=5, and "2/3 basic chlorhydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the antiperspirant gel-solid stick compositions include those which conform to the formula:

$$ZrO(OH)_{2-a}Cl_a \cdot xH_2O$$

wherein a is from about 1.5 to about 1.87; x is from about 1 to about 7; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorhydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, all of which are incorporated herein by reference.

The antiperspirant gel-solid stick compositions of the present invention can also be formulated to comprise other dispersed solids or other materials in addition to or in place of the particulate antiperspirant active. Such other dispersed solids or other materials include any material known or otherwise suitable for topical application to human skin. The antiperspirant gel-solid stick compositions can also be formulated as gel-solid stick compositions which contain no antiperspirant or other active material, particulate or otherwise.

Gellant

The antiperspirant gel-solid stick compositions of the present invention comprise a solid non-polymeric gellant suitable for topical application to human skin, other than inorganic thickening agents, organic polymeric gellants or other gellants such as dibenzylidene alditol and n-acyl amino acid derivatives. These solid non-polymeric gellants must form within the composition a crystalline matrix within which an anhydrous liquid carrier or other liquid component of the composition is trapped or contained. These solid non-polymeric gellants preferably form crystalline particles having an average particle diameter and particle morphology as described hereinafter.

The antiperspirant gel-solid stick compositions are substantially free of inorganic thickening agents, organic polymeric thickening agents, and gellants selected from the group consisting of dibenzylidene alditols, and n-acyl amino acid derivatives. In this context, "substantially free" means that the compositions contain less than an effective amount of such agents that when used alone would provide any thickening or measurable viscosity increase to the composition under ambient conditions. Generally, the compositions preferably contain less than 5%, more preferably less than 1%, even more preferably less than 0.5%, most preferably zero percent, of such agents by weight of the composition.

The antiperspirant gel-solid compositions are preferably substantially free of fatty alcohols that are solids under ambient conditions and which contain from 12 to 40 carbon atoms. More specifically, the compositions herein preferably contain no more than about 5%, preferably from zero to about 2%, by weight of such fatty alcohol materials. Minimal concentrations of such materials may be used, however, in the composition as a nucleating agent as described hereinafter.

The concentration of the gellants in the compositions may vary with each selected antiperspirant gel-solid stick formulation, especially with each selected anhydrous liquid carrier of the formulation, but such concentrations will generally range from about 0.1% to about 20%, preferably from about 1% to about 15%, more preferably from about 3% to about 12%, by weight of the composition. The non-polymeric gellants must be solids under ambient conditions.

The solid non-polymeric gellants for use in the antiperspirant gel-solid stick compositions are those which can melt and form a solution or other homogenous liquid or liquid dispersion with the selected anhydrous liquid carrier, and at the selected gellant and liquid carrier concentrations, at a processing temperature of from about 28° C. to about 250° C., preferably from about 28° C. to about 100° C., more preferably from about 28° C. to about 78° C. The melted non-polymeric gellant is typically dissolved by or dispersed throughout the selected liquid carrier to thus form a solution or other homogenous liquid. The solution or other homogenous liquid, and other essential and optional ingredients, are preferably combined in accordance with the manufacturing method described herein or other conventional or otherwise known technique, and then placed in a suitable package as a flowable solution or homogenous liquid, and then allowed to solidify and form the desired solid gel matrix within the composition as the temperature returns to ambient temperature and drops to below the solidification point of the composition.

In selecting a combination of solid non-polymeric gellant and liquid carrier for use in the antiperspirant gel-solid stick compositions, the selected combination should allow for the development of a crystalline gellant matrix within the composition wherein the component crystalline particles preferably have an average particle size of less than about 1 µm, more preferably less than about 0.4 µm, even more preferably less than about 0.2 µm, most preferably from about 0.001 µm to about 0.2 µm, and/or wherein the crystalline particles have the requisite elongated morphology described herein, wherein particle size is measured or determined by the methods described herein or by methods well-known to those skilled in the art such as light or electron microscopy. The gel-solid stick compositions can be prepared by methods well known in the formulation art for making gel-solids having minimal crystalline particle size or the preferred elongated particle morphology. The gel-solid stick compositions are preferably prepared by the select methods described hereinafter directed to minimizing crystalline particle size and/or establishing the preferred crystalline particle morphology.

Solid non-polymeric gellants suitable for use in the antiperspirant gel-solid stick compositions of the present invention include fatty acid gellants, esters and amides of fatty acid gellants, hydroxy acids, hydroxy fatty acids, cholesterolic materials, lanolinolic materials, and other amide gellants known for use as gelling agents or which are otherwise described in detail hereinafter. Other crystalline gellants can be used in the gel-solid stick compositions of the present invention provided that such other gellants can be formulated to provide the requisite crystalline gel matrix and product and rheology characteristics defined herein.

Other solid non-polymeric gellants suitable for use in the antiperspirant gel-solid stick compositions herein include fatty acid gellants which include, but are not limited to, fatty acid and hydroxy or alpha hydroxy fatty acids, having from about 10 to about 40 carbon atoms, examples of which include 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred fatty acid gellants are those having the fatty acid dimer to monomer ratio as described hereinafter.

Preferred solid non-polymeric gellants suitable for use in the antiperspirant gel-solid stick compositions include 12-hydroxystearic acid, esters of 12-hydroxystearic acid, amides of 12-hydroxystearic acid and combinations thereof. These preferred gellants include those which correspond to the following formula:

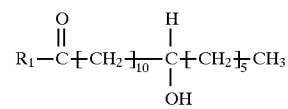

wherein $R_1$ is $OR_2$ or $NR_2R_3$; and $R_2$ and $R_3$ are hydrogen, or an alkyl, aryl, or arylalkyl radical which is branched linear or cyclic and has from about 1 to about 22 carbon atoms; preferably, from about 1 to about 18 carbon atoms. $R_2$ and $R_3$ may be either the same or different; however, at least one is preferably a hydrogen atom. Preferred among these gellants are those selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and mixtures thereof; even more preferably, 12-hydroxystearic acid, isopropyl amide of 12-hydroxystearic acid, and combinations thereof. Most preferred is 12-hydroxystearic acid.

Suitable amide gellants include disubstituted or branched monoamide gellants, monosubstituted or branched diamide gellants, triamide gellants, and combinations thereof, excluding the n-acyl amino acid derivatives selected from the group consisting of n-acyl amino acid amides, n-acyl amino acid esters prepared from glutamic acid, lysine, glutamine, apartic acid, and combinations thereof, and which are specifically disclosed in U.S. Pat. No. 5,429,816.

Preferred amide gellants for use herein include alkyl amides of di- and/or tri-basic carboxylic acids or anhydrides, concentrations of which are preferably from about 0.1% to about 25%, preferably of from about 1% to about 15%, more preferably from about 1% to about 10%, by weight of the composition. Alkyl amides suitable for use in the antiperspirant gel-solid stick compositions herein include those which conform to the formula:

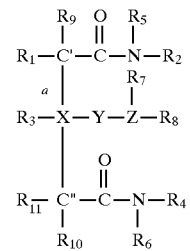

wherein a backbone is formed from the linkage of C', C" and X and wherein a) $R_1$ is nil, hydroxy, hydrogen, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{18}$ alkyl, $C_4$–$C_{18}$ alkenyl, $C_4$–$C_{18}$ alkoxy, $C_4$–$C_{18}$ alkyl esters, $C_4$–$C_{18}$ alkyl ethers, or $C_4$–$C_{18}$ alkyl substituted aryl, more preferably $C_{12}$–$C_{18}$ alkyl, $C_{12}$–$C_{18}$ alkenyl, $C_{12}$–$C_{18}$ alkoxy, $C_{12}$–$C_{18}$ alkyl esters, $C_{12}$–$C_{18}$ alkyl ethers, or $C_{12}$–$C_{18}$ alkyl substituted aryl;

b) $R_2$, $R_4$, $R_5$ and $R6$ are independently or together, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl;

c) $R_3$ is nil, hydroxy, hydrogen, saturated or unsaturated, substituted or unsubstituted, straight, branched or cyclic chain $C_1$–$C_4$ alkyl, $C_1$–$C_4$ alkenyl, $C_1$–$C_4$ alkoxy, $C_1$–$C_4$ alkyl esters or $C_1$–$C_4$ alkyl ethers, preferably a $C_1$–$C_4$ alkoxy, hydroxy or hydrogen, more preferably a hydroxy or hydrogen;

d) $R_7$ and $R_8$ are independently or together, nil, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl;

e) $R_9$ is nil or hydrogen;

f) $R_{10}$ and $R_{11}$ are independently or together, nil, hydrogen, hydroxy, aryl, siloxane or saturated or unsaturated, substituted or unsubstituted, straight, branched or cyclic chain $C_1$–$C_6$ alkyl, $C_1$–$C_6$ alkenyl, $C_1$–$C_6$ alkoxy, $C_1$–$C_6$ alkyl esters, $C_1$–$C_6$ alkyl ethers, or $C_1$–$C_6$ alkyl substituted aryl, preferably $C_1$–$C_4$ alkyl, $C_1$–$C_4$ alkenyl, $C_1$–$C_4$ alkoxy, $C_1$–$C_4$ alkyl esters, $C_1$–$C_4$ alkyl ethers, $C_1$–$C_4$ alkyl substituted aryl or hydrogen, more preferably a hydrogen;

g) X is nil, nitrogen, aryl or $-(CH_2)_n-$ where n is an integer from 1 to 6, preferably $-(CH_2)_n-$ where n is an integer from 1 to 3;

h) Y is nil, acyl or carbonyl;

i) Z is nil, hydrogen, hydroxy, aryl, siloxane, nitrogen or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl; and j) "a" is a double or single bond provided:
  (i) when X is nil, Y, Z, $R_3$, $R_7$ and $R_8$ are nil, C' is bonded directly to C" and $R_1$ is not a hydrogen;
  (ii) when X and Z are not nil and Y is nil, X is directly bonded to Z;
  (iii) when Z is nil, a hydrogen or a hydroxy, $R_7$ and $R_8$ are nil; and
  (iv) when "a" is a double bond, $R_3$ and $R_9$ are nil.

Alkyl amides of di- and tri-basic carboxylic acids or anhydrides suitable for use in the antiperspirant gel-solid stick composition include alkyl amides of citric acid, tricarballylic acid, aconitic acid, nitrilotriacetic acid, succinic acid and itaconic acid such as 1,2,3-propane tributylamide, 2-hydroxy-1,2,3-propane tributylamide, 1-propene- 1,2,3-trioctylamide, N,N',N"-tri(acetodecylamide)amine, 2-dodecyl-N,N'-dihexylsuccinamide, and 2 dodecyl-N,N'-dibutylsuccinamide. Preferred are alkyl amides of di-carboxylic acids such as di-amides of alkyl succinic acids, alkenyl succinic acids, alkyl succinic anhydrides and alkenyl succinic anhydrides, more preferably 2-dodecyl-N, N'-dibutylsuccinamide.

The alkyl amide gelling agents, preferably, have opposing and substantially parallel terminal chains extending outward from the gelling agent backbone. It is believed that this spacial arrangement, or "tuning fork" structural configuration, facilitates the formation of networks essential to the formulation of gel or gel-solid stick compositions. By the phrase "tuning fork configuration", as used herein means any configuration resembling an article or implement having a handle portion which extends longitudinally at one end to form two prongs. It is also preferred that the terminal chains be linked to the gelling agent backbone by means of acyl-amide linkages wherein the acyl portion of the acyl-amide linkage is directly attached to the gelling agent backbone.

The alkyl amides gellants may be synthesized using either of the following one or two step reaction procedures. The one step procedure involves direct amidation of the di- or tri-basic organic acid or anhydride with the appropriate alkyl amine under reaction temperatures typically at or near the boiling point of the alkyl amine, preferably from about 30° C. to about 200° C., followed by removal of excess amine. Certain reactions, do to their exothermic nature, may not require external heating.

The alkyl amides gellants may also be synthesized using a two step procedure which involves esterification of the di- or tri-basic organic acid or anhydride with methanol using a boron trifluoride or other Lewis Acid catalyst at a temperature of from about 30° C. to about 100° C. followed by removal of the excess methanol and catalyst. The resulting trimethyl ester is then amidated as described in the one step process above using the appropriate alkylamine followed by removal of excess amine. The alkyl amides are preferably non-polymeric.

These solid non-polymeric gellants described herein are especially effective when used in combination with select anhydrous carriers such as volatile silicones, especially volatile cyclomethicone. These gellants are most preferably used in combination with a liquid carrier comprising a volatile silicone and a non-volatile silicone (e.g., non-volatile dimethicones or other organofunctional siloxanes well known in the art) and/or a non-volatile organic carrier.

Preferred Enantomeric Gellants

Preferred solid non-polymeric gellants for use herein include those enantomeric compounds or materials containing at least one asymmetric (chiral) carbon atom. Non-limiting examples of these preferred enantomeric gellants include 12-hydroxystearic acid, other hydroxy acids such as alpha hydroxy acids, cholesterols, lanolin, and derivatives thereof It has been found that these preferred enantomeric gellants, when used in the anhydrous antiperspirant gel-solid stick compositions herein, provide the composition with the requisite product hardness, visible residue index values and rheological properties (G'/G"). It is believed that these enantomeric gellants are especially effective in forming one-dimensional elongated particles in the form of filaments, fibrils or strings which are intertwined or twisted to form a stable, three-dimensional crystalline matrix in the gel-solid composition. These elongated particles have an aspect ratio of greater than about 2, preferably greater than about 6. It is believed that these gellants form elongated crystalline particles that result in a stable crystalline matrix that, in part because of the small size and elongated morphology of these particles, cause less scattering of light when applied to the skin in the antiperspirant composition, which then results in low visible residue after such application.

Preferred Particle Morphology

The solid non-polymeric gellants for use herein include those crystalline gellants that inherently form, or can be formulated or otherwise made to form, elongated crystalline particles having an aspect ratio greater than about 2, preferably greater than about 6. These elongated crystals preferably have an average particle size as measured along a minor axis of the elongated crystal of less than 1 $\mu$m, more preferably less than about 0.4 $\mu$m, even more preferably less than about 0.2 $\mu$m, most preferably from about 0.2 $\mu$m to about 0.001 $\mu$m.

The gel-solid stick compositions containing these preferred elongated crystals can be prepared by methods described herein, or by methods otherwise known in the formulation art for formulating gel matrices comprising these elongated crystalline particles.

The "aspect ratio" as used herein to define preferred embodiments of the gel-solid stick compositions herein can be determined by measuring or otherwise determining the ratio of the length of the major axis of the crystalline particles to the length of the minor axis of the crystalline particles. This length ratio of the major to minor axis is characterized as the aspect ratio referred to herein. The aspect ratio can be determined by conventional or otherwise known light or electron microscopy methods, wherein the crystalline particles are measured for major and minor axis dimensions, or are otherwise observed by such methods to clearly have an apparent elongated crystalline structure with an aspect ratio substantially greater than about 2, preferably greater than about 6.

It has been found that these crystalline gellants having the select aspect ratios defined herein, provide the antiperspirant gel-solid stick compositions a three-dimensional crystalline structure that can provide the composition with the requisite low residue performance, elastic to viscous moduli ratio, and product hardness as defined herein. It is believed that this crystalline morphology is especially effective in providing a crystalline matrix within the composition that provides for a strong interlocking gel-solid matrix network, but which also comprises crystalline particles that are sufficiently small in size so as to contribute minimally to visible residue when applied topically to the skin.

It has also been found that the preferred crystalline matrix helps provide the gel-solid stick compositions with a melt profile that contributes to low residue performance. This preferred melt profile refers to the temperature at which the antiperspirant gel-solid stick composition begins to melt, and the temperature range within which the composition is completely melted, except for any dispersed antiperspirant particulates or other high melting point components. The temperature at which the composition begins to melt is determined by measuring a Differential Scanning Calorimeter (DSC) onset temperature. The temperature range within which the composition is completely melted is determined by no additional heat infusion. Preferred embodiments of the gel-solid stick compositions herein have a DSC onset temperature of from about 25° C. to about 85° C., preferably from about 27° C. to about 65° C., more preferably from about 30° C. to about 60° C., even more preferably from about 35° C. to about 50° C. These preferred compositions having the select melt profile provide improved cosmetics or aesthetics when applied topically to the skin, and especially provide reduced feeling of wetness, stickiness or product softness during and immediately after application. The select melt profile also helps to further reduce the visible residue index of the composition, thus further improving lower residue performance.

Preferred Dimer to Monomer Ratio

The solid non-polymeric gellant of the antiperspirant gel-solid stick compositions herein preferably comprise a fatty acid gellant having a select dimer-to-monomer ratio. The fatty acid gellants having the requisite dimer-to-monomer ratio may be used alone or in combination with an additional or secondary gellant in the composition. The select dimer-to-monomer ratio helps provide the gel-solid stick compositions herein with improved low residue performance, efficacy and aesthetics, and especially provides for improved low residue performance and improved product hardness.

The fatty acid gellants in the antiperspirant gel-solid stick composition, when used in combination with an additional or secondary gellant, has a select dimer-to-monomer ratio of from about 1:1 to about 25:1, preferably from about 1.5:1 to about 25:1, more preferably from about 2.5:1 to about 20:1, even more preferably from about 3:1 to about 10:1. The higher dimer-to-monomer ratios are preferred.

The dimer-to-monomer ratio of the fatty acid gellant can be determined by methods or techniques known in the formulation arts, including infrared methods such as Fourier Transform Infared (FTIR) Spectroscopy. Such methods are disclosed in *The Infared Spectra of Complex Molecules*, L. J. Bellamy, 2nd Edition, 1958, *Introduction to Infared and Raman Spectroscopy*, N. B. Colthup, et. al., 3rd Edition, 1990, and *Fourier Transform Infared Spectroscopy*, P. R. Griffiths, et. al., 1986, all disclosures of which are incorporated by reference herein. In accordance with such methods or techniques, fatty acids are usually characterized by their carbonyl stretching frequencies which are measured as absorption bands between 1740 cm$^{-1}$ and 1680 cm$^{-1}$. The fatty acid gellant of the antiperspirant composition of the present invention comprises fatty acid dimers and fatty acid monomers which are components of the carbonyl absorption band. However, due to the formation of hydrogen bonded dimers, the fatty acid dimer component can be shifted as far as 30 cm$^{-1}$ frequencies lower than the fatty acid monomer frequency.

By use of infrared spectra data, the dimer-to-monomer ratio is determined by calculating the ratio of the peak area of the hydrogen bonded dimer second derivative band near 1696 cm$^{-1}$ to the peak area of the fatty acid monomer second derivative band near 1712 cm$^{-1}$. In accordance with the following methodology, an infrared spectra is recorded using a 45° ZnSe Attenuated Total Reflectance ("ATR" herein) crystal and a horizontal ATR apparatus (available from Spectra Tech, Inc., Shelton, Conn., U.S.A.) attached to a Nicolet 20scx FTIR Spectrometer. The Nicolet 20scx FTIR Spectrometer is available from Nicolet Instrument Corporation, Madison, Wis., U.S.A. The Nicolet 205scx FTIR Spectrometer is equipped with a narrow band mercury cadmium Telluride detector whereby an average of 256 scans are co-added to generate the infrared spectra. The infrared spectra is then imported into a computer software program such as GRAMS/386 (available from Galactic Industries Corporation, Salem, N.H., U.S.A.) to calculate the dimer-to-monomer ratio using a 5 point second derivative algorithm which is a mathematical procedure defined by Savitsky-Golay.

The requisite dimer-to-monomer ratio may be established with the fatty acid gellants described herein, which includes alpha-hydroxy fatty acids and fatty acids having from about 10 to about 40 carbon atoms, examples of which include 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Examples of some suitable fatty acid gellants are described in U.S. Pat. No. 5,429,816, issued to Hofrichter et al. on Jul. 4, 1995; and U.S. Pat. No. 5,552,136, issued to Motley on Sep. 3, 1996, which descriptions are incorporated herein by reference. Most preferred is 12-hydroxystearic acid.

The requisite dimer-to-monomer ratio may also be established with the fatty acid gellants described herein in combination with an additional or secondary gellant, wherein the molar ratio of the fatty acid gellant to the additional or secondary gellant is from about 1:2 to about 20:1, preferably from about 1:1 to about 10:1, more preferably from about 2:1 to about 7:1, and even more preferably from about 3:1 to about 5:1. One of average skill in the chemical or formulation arts can formulate these fatty acid gellant systems to control or otherwise obtain the desired ratio. The additional or secondary gellants suitable for use in formulating the requisite dimer-to-monomer ratio include the other solid non-polymeric gellants described herein.

Anhydrous Liquid Carrier

The anhydrous antiperspirant gel-solid stick compositions of the present invention comprise an anhydrous carrier which is liquid under ambient conditions, and which contains a modified silicone carrier selected from the group consisting of polyalkylsiloxanes, polyalkyarylsiloxanes, polyestersiloxanes, polyethersiloxane copolymers, polyfluorosiloxanes, polyaminosiloxanes, and combinations thereof.

Concentrations of the anhydrous liquid carrier in the gel-solid stick composition will vary primarily with the type and amount of the anhydrous liquid carrier, the solid non-polymeric gellant, and the solubility of the solid non-polymeric gellant in the anhydrous liquid carrier. Preferred concentrations of the anhydrous liquid carrier are from about 10% to about 80%, preferably from about 30% to about 70%, more preferably from about 45% to about 70%, by weight of the composition. Concentrations of the modified silicone carrier component of the anhydrous liquid carrier is from about 0.1% to about 80%, preferably from about 0.1% to about 50%, more preferably from about 1% to about 20%, and even more preferably from about 1% to about 10%, by weight of the antiperspirant gel-solid stick composition.

The anhydrous liquid carrier preferably comprises one or more other carrier liquids other than and in addition to the modified silicone carriers described herein. These other carrier liquids should be suitable for topical application to human skin, and may include organic or silicone-containing or fluorine-containing, volatile or non-volatile, polar or non-polar, carrier liquids, provided that the resulting anhydrous liquid carrier forms a solution or other homogenous liquid or liquid dispersion with the selected non-polymeric gellant at the selected gellant concentration at a temperature of from about 28° C. to about 250° C., preferably from about 28° C. to about 100° C., preferably from about 28° C. to about 78° C.

The anhydrous liquid carrier has a solubility parameter of from about 3 to about 13 $(cal/cm^3)^{0.5}$, preferably from about 5 to about 11 $(cal/cm^3)^{0.5}$, more preferably from about 5 to about 9 $(cal/cm^3)^{0.5}$. Solubility parameters for the liquid carriers or other materials, and means for determining such parameters, are well known in the chemical arts. A description of solubility parameters and means for determining them are described by C. D. Vaughan, "Solubility Effects in Product, Package, Penetration and Preservation" 103 Cosmetics and Toiletries 47–69, October 1988; and C. D. Vaughan, "Using Solubility Parameters in Cosmetics Formulation", 36 J. Soc. Cosmetic Chemists 319–333, September/October, 1988, which descriptions are incorporated herein by reference.

These modified silicone carriers for use in the antiperspirant gel-solid stick composition must be liquid under ambient conditions, and have a viscosity of less than about 100,000 centistokes, preferably less than about 500 centistokes, more preferably from about 1 centistoke to about 50 centistokes, and even more preferably from about 1 centistoke to about 20 centistokes. These modified silicone carriers are generally known in the chemical arts, some examples of which are described in 1 *Cosmetics, Science and Technology* 27–104 (M. Balsam and E. Sagarin ed. 1972); U.S. Pat. No. 4,202,879, issued to Shelton on May 13, 1980; U.S. Pat. No. 5,069,897, issued to Orr on Dec. 3, 1991; which descriptions are incorporated herein by reference.

The modified silicone carriers suitable for use in the antiperspirant gel-solid stick compositions include, but are not limited to, compounds or materials as defined hereinabove and which are generally characterized as follows: silicone polyethers or silicone glycols (such as dimethicone copolyol); silicone alkyl-linked polyethers (such as Goldschmidt EM-90 or EM-97); siloxane surfactants of a pendant/rake/comb configuration, silicone surfactants of a trisiloxane configuration, and silicone surfactants of an ABA/alpha-omega block copolymers (such as polyoxyalkylenes, polyoxyethylene or ethoxylated, polyoxyethylene/polyoxypropylene or ethoxylated/propoxylated); aromatic substituted silicone emollients (such as phenyl, alpha-methyl styryl, styryl, methylphenyl, alkylphenyl); silicone copolymers with other functional groups include: hydrogen, alkyl, methyl, amino, trifluoropropyl, vinyl, alkoxy, arylalkyl, aryl, phenyl, styryl, polyethers, esters, carboxylics; alkylmethyl siloxanes or silicone waxes (such as hexyl, octyl, lauryl, cetyl, stearyl); nonionic functional siloxane copolymers with terminal groups being silanol or trimethylsiloxy; nonionic functional siloxanes with backbone groups being trisiloxane or methicone linked; nonionic silicone surfactants; tetraethoxysilane; tetramethoxysilane; hexamethoxysilicone; oxmethoxytrisiloxane; silicone emulsifiers; silicone or siloxane resins, alkyl silicone resins, polyoxyalkylene silicone resins; MQ Resins such as Shiseido/Shin-etsu, e.g. Japanese Patent Publication JP86143760 or from Walker Chem. 6MBH (described in EP722970); alkoxysiloxanes; alkoxysilanes; methicones (polymethylalkylsiloxanes); and combinations thereof.

Nonlimiting examples of suitable modified silicone carriers for use in the antiperspirant gel-solid stick compositions herein include the following modified silicones available from Dow Corning: DC-556 Cosmetic Grade Fluid (phenyl trimethicone); DC-704 Diffusion Pump Fluid (Tetramethyl-Tetraphenyl-Trisiloxane); DC-705 Diffusion Pump Fluid; DC-1784 Emulsion; DC-AF Emulsion; DC-1520-US Emulsion; DC-593 Fluid (Dimethicone [and] Trimethylsiloxysilicate); DC-3225C Fluid (Cyclomethicone [and] Dimethicone Copolyol); DC-190 Fluid (Dimethicone Copolyol); DC-193 Fluid (Dimethicone Copolyol); DC-1401 (Cyclomethicone [and] Dimethiconol); DC-5200 Fluid (Laurylmethicone Copolyol); DC-6603 Polymer Powder; DC-5640 Powder; DC-Q2-5220 (Dimethicone Copolyol); DC Q2-5324 (Dimethicone Copolyol); DC-2501 Cosmetic Wax (Dimethicone Copolyol); DC-2502 Fluid (Cetyl Dimethicone); DC-2503 Wax (Stearyl Dimethicone); DC-1731 Volatile Fluid (Caproyl Trimethicone); DC-580 Wax (Stearoxytrimethylsilane [and] Stearyl Alcohol); DC-1-3563 (Dimethiconal); DC-X2-1286 (Dimethiconol); DC-X2-1146A (Cylcomethicone [and] Dimethiconol); DC-8820 Fluid (Amino functionalized); DC Q5-0158A wax (stearoxytrimethylsilane); DC-Q2-8220 (Trimethylsilylamodimethicone); DC-7224 (Trimethylsilylamodimethicone); DC-X2-1318 Fluid (Cyclomethicone [and] Vinyldimethicone); DC-QF1-3593A fluid (Trimethylsiloxysilicate) and combinations thereof.

Other nonlimiting examples of suitable modified silicone carriers for use in the antiperspirant gel-solid stick compositions herein include the following modified silicones available from General Electric: GE SF-1023 (Dimethyl-Diphenyl-Siloxane); GE CF-1142 (Methylphenyl Siloxane Fluid); GE SF-1153 (Dimethyl-Diphenyl-Siloxane); GE SF-1265 (Diphenyl-Dimethyl-Siloxane); GE SF-1328; GE SF-1188 (Dimethicone copolyol); GE SF-1188A (Silicone polyether copolymer); GE SF-1288 (silicone polyether copolymer, dimethyl-methyl 3-hydroxypropyl ethoxylated); GE SF-1318 (Methylester Siloxane); GE SF-1328 (silicone surfactant, dimethyl-methyl 3-hydroxypropyl ethoxylated-propoxylated); GE SF-1550 (methylphenyl siloxane, hexamethyl-3-phenyl-3-[[trimethylsilyl]oxy]trisiloxane); GE SF-1632 (silicone wax); GE SS-4267 (Dimethicone [and] Trimethylsiloxysilicate) and combinations thereof.

Other nonlimiting examples of suitable modified silicone carriers for use in the antiperspirant gel-solid stick compositions herein include the following modified silicones available from Goldschmidt: Abil EM-90 (silicone emulsifier); Abil EM-97 (polyether siloxane); Abil Wax 9810 (silicone wax or C24-28 methicone); Abil Wax 2434 (Stearoxy Dimethicone); Abil Wax 9800D (Stearyl Dimethicone); Tegomer H-Si 2111, H-Si 2311, A-Si 2120, A-Si 2320, C-Si 2141, C-Si 2341, E-Si 2130, E-Si 2330, V-Si 2150, V-Si 2550, H-Si 6420, H-Si 6440, H-Si 6460 (Alpha-Omega Dimethicone Copolymers) and combinations thereof.

Other nonlimiting examples of suitable modified silicone carriers for use in the antiperspirant gel-solid stick compositions herein include the following: Masil 756 from PPG Industries (Tetrabutoxypropyl Trisiloxane); bis-phenylhexamethicone (available as Silbione Oils 70633 V30 from Rhone-Poulenc); Silbione Oils 70646 (dimethicone copolyols from Rhone-Poulenc); Silicone L-711, L-720, L-721 and L722 (dimethicone copolyols from Union Carbide); Silicone L-7000, L-7001, L-7002, L-7004, L-7500, L-7600, L-7602, L-7604, L-7605, and L-7610 (dimethicone copolyols from Union Carbide); Unisil SF-R (dimethiconol from UPI); Silicate Cluster from Olin (Tris [tributoxysiloxy]methylsilane); silicone copolymer F-754 (dimethicone copoly from SWS Silicones); and combinations thereof.

The anhydrous liquid carrier preferably comprises a volatile silicone carrier in combination with the modified silicone carrier. These volatile silicone carriers may be cyclic, linear or branched chain silicones having the requisite volatility defined herein. Non-limiting examples of suitable volatile silicones are described in Todd et al., "Volatile Silicone Fluids for Cosmetics", Cosmetics and Toiletries, 91:27–32 (1976), which descriptions are incorporated herein by reference. Preferred among these volatile silicones are the cyclic silicones having from about 3 to about 7, more preferably from about 4 to about 5, silicon atoms. Most preferably are those which conform to the formula:

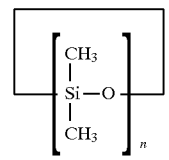

wherein n is from about 3 to about 7, preferably from about 4 to about 5, most preferably 5. These volatile cyclic silicones generally have a viscosity value of less than about 10 centistokes. All viscosity values described herein are measured or determined under ambient conditions, unless otherwise specified. Suitable volatile silicones for use herein include, but are not limited to, Cyclomethicone D-5 (commercially available from G. E. Silicones); Dow Corning 344, and Dow Corning 345 (commercially available from Dow Corning Corp.); GE 7207, GE 7158 and Silicone Fluids SF-1202 and SF-1173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof.

The anhydrous liquid carrier may also comprise a non-volatile silicone carrier in combination with the modified silicone carriers described hereinbefore. These non-volatile silicone carriers are preferably linear silicones which include, but are not limited to, those which conform to either of the formulas:

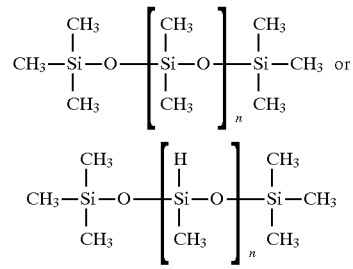

wherein n is greater than or equal to 1. These linear silicone materials will generally have viscosity values of up to about 100,000 centistoke, preferably less than about 500 centistoke, more preferably from about 1 centistoke to about 200 centistoke, even more preferably from about 1 centistoke to about 50 centistoke, as measured under ambient conditions. Examples of non-volatile, linear silicones suitable for use in the antiperspirant compositions include, but are not limited to, Dow Corning 200, hexamethyldisiloxane, Rhodorsil Oils 70047 available from Rhone-Poulenc, Masil SF Fluid available from Mazer, Dow Corning 225, Dow Corning 1732, Dow Corning 5732, Dow Corning 5750 (available from Dow Corning Corp.); SF-96, SF-1066 and SF18(350) Silicone Fluids (available from G. E. Silicones); Velvasil and Viscasil (available from General Electric Co.); and Silicone L-45, Silicone L530, Silicone L-531 (available from Union Carbide), and Siloxane F-221 and Silicone Fluid SWS-101 (available from SWS Silicones).

The anhydrous liquid carrier may further comprise, but is preferably substantially free of, organic, water-immiscible, polar liquid carriers or solvents in combination with the modified silicone carrier. It has been found that the antiperspirant and deodorant efficacy of the gel-solid stick compositions are improved by minimizing or eliminating the amount or concentration of these polar, organic, water-immiscible, liquid carriers or solvents in the composition. In this context, the term "substantially free" means that the antiperspirant gel-solid stick compositions preferably contain less than 7%, more preferably less than about 3%, even more preferably zero percent, by weight of an organic, water-immiscible, polar liquid carrier or solvent. These organic polar solvents are liquid under ambient conditions and include mono and polyhydric alcohols, fatty acids, esters of mono and dibasic carboxylic acids with mono and polyhydric alcohols, polyoxyethylenes, polyoxypropylenes, polyalkoxylates ethers of alcohols, and combinations thereof, provided that such solvents are also water-immiscible liquids under ambient conditions. Examples of some organic, water-immiscible, polar liquid carriers or solvents are described in Cosmetics, Science, and Technology, Vol. 1, 27–104, edited by Balsam and Sagarin (1972); U.S. Pat. No. 4,202,879 issued to Shelton on May 13, 1980; and U.S. Pat. No. 4,816,261 issued to Luebbe et al. on March 28, 1989, which descriptions are incorporated herein by reference.

The anhydrous liquid carrier may also comprise an anhydrous, water-miscible, polar organic liquid carrier or solvent in combination with the modified silicone carrier, examples of which include short chain alcohols such as ethanol. These and other polar organic carriers or solvents can be used as co-solvents for the solid non-polymeric gellant component of the antiperspirant gel-solid stick compositions herein. Non-limiting examples of polar co-solvents suitable for use herein are described in U.S. Pat. No. 5,429,816. Other suitable polar co-solvents include those described hereinabove, which are preferably water-immiscible organic solvents, and other co-solvents such as phthalate co-solvents, benzoate co-solvents, cinnamate esters, secondary alcohols, benzyl acetate, phenyl alkane and combinations thereof.

The anhydrous liquid carrier may also comprise other non-polar carriers in combination with the modified silicone carrier. Examples of such other non-polar carriers include mineral oil, petrolatum, isohexadecane, isododecane, various hydrocarbon oils such as the Isopar or Norpar series available from Exxon Corp. or Permethyl series available from Persperse, and any other polar or non-polar, water-miscible, organic carrier liquid or solvent known or otherwise safe and effective for topical application to human skin.

The anhydrous liquid carrier may also comprise fluorochemicals in addition to or in place of the modified silicone carrier. These fluorochemicals include fluorosurfactants, fluorotelemers, and perfluoropolyethers, some examples of which are described in Cosmetics & Toiletries, Using Fluorinated Compounds in Topical Preparations, Vol. 111, pages 47–62, (October 1996) which description is incorporated herein by reference. More specific examples of such liquid carriers include, but are not limited to, perfluoropolymethyl isopropyl ethers, perfluoropolypropylethers, acrylamide fluorinated telomer, fluorinated amide surfactants, perfluorinated thiol surfactants. Other more specific examples include, but are not limited to, the polyperfluoroisopropyl ethers available from Dupont Performance Chemicals under the trade name Fluortress® PFPE oils, and the series fluorosurfactants from Dupont Performance Chemicals under the trade name Zonyl® Fluorosurfactants.

Optional Nucleating Agent

The antiperspirant gel-solid stick compositions of the present invention preferably further comprises a nucleating agent. The nucleating agent is used to minimize gellant particle size, and/or for obtaining the preferred gellant particle morphology described herein.

The nucleating agent for use in the antiperspirant composition of the present invention must be a solid material under ambient conditions and have 1) a melting point near the melting point of the selected gellant, 2) a solubility in the anhydrous liquid carrier that is less than the solubility of the solid non-polymeric gellant in the anhydrous liquid carrier, or 3) be in the form of an inorganic, insoluble, micronized particulate. Examples of suitable nucleating agents are described hereinafter.

The concentration of the nucleating agent in the composition is typically from about 0.0001% to about 5%, preferably from about 0.001% to about 2%, more preferably from about 0.01% to about 1%, wherein the molar ratio of the solid non-polymeric gellant to the nucleating agent is from about 10:1 to about 1000:1, preferably from about 10:1 to about 100:1. Preferred nucleating agents are those having a melt point of from about 40° C. below to about 200° C. above, more preferably from about 20° C. below to about 100° C. above, the melting point of the selected solid non-polymeric gellant.

The antiperspirant compositions containing the nucleating agent are preferably prepared by 1) combining the solid non-polymeric gellant, anhydrous liquid carrier and a nucleating agent as described herein, 2) heating components or the combination of components to form a solution or other homogeneous liquid or liquid dispersion, and 3) solidifying the combination of components by cooling the combination to below the solidification point of the solid non-polymeric gellant to form the antiperspirant composition of the present invention. During this process, the solid non-polymeric gellant is preferably melted or otherwise liquefied, and then allowed to solidify in the presence of the anhydrous liquid carrier and the nucleating agent. Also during this process, the nucleating agent is typically melted or otherwise liquefied (except for micronized, inorganic nucleating agents), and then in the presence of the anhydrous liquid carrier and the melted or liquefied gellant, the liquified nucleating agent crystallizes, gels or otherwise solidifies and acts as a seed or nucleus to promote formation of small gellant nuclei during the crystallization of the gellant in the anhydrous liquid carrier.

The nucleating agent for use in the antiperspirant compositions include fatty alcohols, esters of fatty alcohols, ethoxylated fatty alcohols, esters or ethers of fatty acids including waxes, and triglycerides, silica, titanium dioxide, solid polyol carboxylic acid polyesters, and mixtures thereof.

Suitable fatty alcohols for use as nucleating agents include monohydric alcohols, ethoxylated fatty alcohols, and fatty alcohol esters. Specific examples of commercially available fatty alcohol nucleating agents include, but are not limited to, Unilin 550, Unilin 700, Unilin 425, Unilin 400, Unilin 350, and Unilin 325, all supplied by Petrolite. Suitable ethoxylated fatty alcohols include, but are not limited, Unithox 325, Unithox 400, and Unithox 450, Unithox 480, Unithox 520, Unithox 550, Unithox 720, Unithox 750, all of which are available from Petrolite. Non-limiting examples of suitable esters of fatty alcohols include tri-isostearyl citrate, ethyleneglycol di-12-hydroxystearate, tristearylcitrate, stearyl octanoate, stearyl heptanoate, trilaurylcitrate.

Suitable fatty acid esters for use as nucleating agents include ester waxes, monoglycerides, diglycerides, triglycerides and mixtures thereof. Preferred are the glyceride esters. Non-limiting examples of suitable ester waxes include stearyl stearate, stearyl behenate, palmityl stearate, stearyl octyldodecanol, cetyl esters, cetearyl behenate, behenyl behenate, ethylene glycol distearate, ethylene glycol dipalmitate, and beeswax. Examples of commercial ester waxes include Kester waxes from Koster Keunen, Crodamol SS from Croda and Demalcare SPS from Rhone Poulenc.

Preferred triglyceride nucleating agents include, but are not limited to, tristearin, tribehenate, behenyl palmityl behenyl triglyceride, palmityl stearyl palmityl triglyceride, hydrogenated vegetable oil, hydrogenated rape seed oil, castor wax, fish oils, tripalmiten, Syncrowax HRC and Syncrowax HGL-C (Syncrowax is available from Croda, Inc.). Other suitable glycerides include, but are not limited to, glyceryl stearate and glyceryl distearate.

Preferably, the nucleating agent is a solid polyol carboxylic acid polyester. Suitable solid polyol carboxylic acid polyesters include those which are polyol esters or polyesters wherein the carboxylic acid ester groups of the polyester comprise a combination of: (a) long chain unsaturated carboxylic acid moieties or a mixture of long chain unsaturated carboxylic acid moieties and short chain saturated carboxylic acid moieties, and (b) long chain saturated carboxylic acid moieties, the ratio of (a) to (b) being from about 1 to 15 to about 2 to 1. At least about 15%, preferably at least about 30%, more preferably at least about 50%, and most preferably at least about 60% by weight of the total carboxylic acid moieties of the polyesters are C20 or higher saturated carboxylic acid moieties. The long chain unsaturated carboxylic acid moieties are typically straight chain and contain at least about 12, preferably about 12 to about 26, more preferably about 18 to about 22 carbon atoms. The most preferred unsaturated carboxylic acids are the C18 mono and/or di unsaturated carboxylic acids. The short chain saturated carboxylic acids are typically unbranched and contain about 2 to about 12, preferably about 6 to about 12, and most preferably about 8 to about 12 carbon atoms. The long chain saturated carboxylic acids are typically straight chain and contain at least about 20, preferably about 20 to about 26, and most preferably about 22 carbon atoms. The molar ratio of Group (a) carboxylic acid moieties to Group (b) carboxylic acid moieties in the polyester molecule is from about 1:15 to about 2:1, preferably about 1:7 to about 5:3, and more preferably about 1:7 to about 3:5. The average degree of esterification of these carboxylic acid esters is such that at least about 2 of the hydroxyl groups of the polyol are esterified. In the case of sucrose polyesters from about 7 to about 8 of the hydroxyl groups of the polyol are preferably esterified. Typically, substantially all, e.g., at least about 85%, preferably at least about 95%, of the hydroxyl groups of the polyol are esterified.

Preferred polyols of the solid polyol carboxylic acid esters are sugars, including monosaccharides and disaccharides and trisaccharides, containing from about 4 to about 11 hydroxyl groups. Most preferred sugars are those which contain about 4 to about 8, more preferably about 6 to about 8 hydroxyl groups. Examples of those containing four hydroxyl groups are the monosaccharides xylose, arabinose, and combinations thereof. Suitable five hydroxyl group-containing polyols are the monosaccharides galactose, fructose, mannose, glucose, and combinations thereof. Examples of disaccharide polyols which can be used include maltose, lactose, sucrose, and combinations thereof, all of which contain eight hydroxyl groups. The preferred polyol is sucrose.

Examples of long chain unsaturated carboxylic acid moieties include, but are not limited to, lauroleate, myristoleate, palmitoleate, oleate, elaidate, erucate, linoleate, linolenate, arachidonate, eicosapentaentoate, and docosahexaenoate. For oxidative stability, the mono- and diunsaturated fatty acid moieties are preferred.

Examples of suitable short chain saturated carboxylic acid moieties include, but are not limited to, acetate, caproate, caprylate, caprate, and laurate.

Examples of suitable long chain saturated carboxylic acid moieties include, but are not limited to, arachidate, behenate, lignocerate, and cerotate.

Of course, the long chain unsaturated carboxylic acid moieties can be used singly or in mixtures with each other or in mixtures with the short chain saturated carboxylic acid moieties, in all proportions. Likewise, the long chain saturated carboxylic acid moieties can be used in combination with each other in all proportions. Mixed carboxylic acid moieties from source oils which contain substantial amounts of the desired unsaturated or saturated acids can be used as the acid moieties to prepare compounds for use as nucleating agents herein. The mixed carboxylic acids from the oils should contain at least about 30%, preferably at least about 50%, and most preferably at least about 80% of the desired unsaturated or saturated acids. For example, rapeseed oil fatty acids or soybean oil fatty acids can be used instead of pure C12–C16 unsaturated fatty acids. Hardened, i.e. hydrogenated, high erucic rapeseed oil fatty acids can be used instead of pure C20–C26 saturated acids, Preferably the C20 and higher acids, or their derivatives, e.g. methyl or other low alkyl esters, are concentrated for example by distillation. The fatty acids from palm kernal oil or coconut oil can be used as a source of C8 to C12 acids. An example of the use of source oils to make solid polyol polyesters for use in the antiperspirant compositions herein is the preparation of solid sucrose polyester, employing the fatty acids of high oleic sunflower oil and substantially completely hydrogenated high erucic rapeseed oil. When sucrose is substantially completely esterified with a 1:3 by weight blend of the methyl esters of the fatty acids of these two oils, the resulting sucrose polyester will have a molar ratio of unsaturated C18 acid radicals to C20 and higher saturated acid radicals of about 1:1 and about 28.6 weight percent of the total fatty acids in the polyester will be C22 fatty acids.

The higher the proportions of the desired unsaturated and saturated acids in the carboxylic acid stocks used in making the solid polyol polyester, the more efficient the ester will be in its ability to function as a nucleating agent.

Examples of solid polyol carboxylic acid polyester nucleating agents for use in the antiperspirant composition herein include, but are not limited to, the octaester of raffinose in which the esterifying carboxylic acid moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterfying carboxylic acid moieties are laurate, linoleate and behenate in a 1:3:4 molar ratio. A preferred material is sucrose polyester in which the degree of esterification is 7–8, and in which the fatty acid moieties are C18 mono- and/or di-unsaturated and behenic, in a molar ratio of unsaturates-:behenic of 1:7 to 3:5. A particularly preferred polyol ester nucleating agent is the octaester of sucrose in which there are about 7 behenic fatty acid moieties and about 1 oleic moiety in the molecule.

The solid carboxylic acid polyesters herein can be made according to prior art known methods for preparing polyesters of polyols. See, for example U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al., issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

Suitable inorganic, micronized, non-solubilized nucleating agents for use in the antiperspirant compositions include materials such as silica, titanium dioxide and combinations thereof. These materials contain submicron particles (average particle size generally less than about 1 $\mu$m) which aid in the production of small gellant crystals or particles.

Preferred nucleating agents, and preferred concentrations of the nucleating agents, for use in the antiperspirant compositions include C18 succinic acid (0.1%), 1,9-nonanedioc acid (0.1%), Teflon (0.1%), silica (0.1%), polysiloxane copolymer (2%), sucrose octabehenate (0.5%, 0.75%, 1.0%), Unilin 350 (0.1%), Unilin 550 (0.1%), Unilin 700 (0.1%), trihydroxystearin (0.1%) and combinations thereof.

Optional Components

The antiperspirant gel-solid stick compositions of the present invention may further comprise one or more optional components which may modify the physical, chemical or aesthetic characteristics of the compositions or serve as additional "active" components when deposited on the skin. The compositions may also further comprise optional inert ingredients. Many such optional materials are known in the antiperspirant art and may be used in the antiperspirant compositions herein, provided that such optional materials are compatible with the essential materials described herein, or do not otherwise unduly impair product performance.

Non-limiting examples of optional materials include active components such as bacteriostats and fungiostats, and "non-active" components such as colorants, perfumes, emulsifiers, chelants, distributing agents, preservatives, residue masking agents, process aides such as viscosity modifiers, and wash-off aids. Examples of such optional materials are described in U.S. Pat. No. 4,049,792, Elsnau, issued Sep. 20, 1977; Canadian Patent 1,164,347, Beckmeyer et al., issued Mar. 27, 1984; U.S. Pat. No. 5,019,375, Tanner et al., issued May 28, 1991; and U.S. Pat. No. 5,429,816, Hofrichter et al., issued Jul. 4, 1995; which descriptions are incorporated herein by reference.

The antiperspirant gel-solid stick compositions of the present invention can also be formulated to comprise other dispersed solids or other materials in addition to or in place of the particulate antiperspirant active. Such other dispersed solids or other materials include any material known or otherwise suitable for topical application to human skin. The antiperspirant gel-solid stick compositions can also be formulated as gel-solid stick compositions which contain no antiperspirant or other active material, particulate or otherwise.

Method of Manufacture

The antiperspirant gel-solid stick compositions of the present invention may be prepared by any known or otherwise effective technique, suitable for providing an antiperspirant gel-solid stick composition having the requisite crystalline matrix and other product characteristics described herein. Such methods involve formulation of the essential components of the composition to form a gel-solid having the requisite elastic to viscous moduli ratio, product hardness, and visible residue index, wherein the crystalline matrix within the composition comprises elongated non-polymeric gellant crystals having an aspect ratio of greater than about 2, preferably greater than about 6, and an average particle diameter that is minimized (preferably to less than about 1 $\mu$m) through techniques directed to minimizing crystalline particle size in a composition.

Crystalline particle size in the preferred embodiments of the present invention can be determined by techniques well known in the art, which includes light or electron microscopy of the composition, wherein the composition is formulated for analysis purposes without particulate antiperspirant active or other solid particulates. Without such reformulation, it is more difficult to directly determine and distinguish crystalline gellant particle size and morphology from the particle size and morphology contributed from other non-gellant particulates. The reformulated composition is then evaluated by light or electron microscopy or other similar method.

Techniques for preparing the antiperspirant gel-solid stick compositions of the present invention include those methods suitable for formulating compositions containing small gellant crystalline particles. Suitable techniques for minimizing crystalline gellant particle size include the use of nucleating agents, formulation with select carriers or gellants or carrier/gellant combinations, controlling rates of crystallization including controlling formulation, controlling process flow rate, and processing temperatures, and other methods described herein. All such methods should be applied to the formulation to control or minimize gellant crystal particle size, and/or to form the desired elongated crystalline particles, to thus form the desired crystalline matrix of the composition.

Method of Use

The antiperspirant gel-solid stick compositions may be applied topically to the axilla or other area of the skin in an amount effective to treat or reduce perspiration wetness and malodor. The composition is preferably applied in an amount ranging from about 0.1 gram to about 20 grams, more preferably from about 0.1 gram to about 10 grams, even more preferably from about 0.1 gram to about 1 gram, to the desired area of the skin. The compositions are preferably applied to the axilla or other area of the skin, one or two times daily, preferably once daily, to achieve effective antiperspirant and malodor control over an extended period.

EXAMPLES

The following non-limiting examples illustrate specific embodiments of the antiperspirant gel-solid stick compositions of the present invention, including methods of manufacture and use.

Each of the exemplified compositions are prepared by combining all of the listed components except the antiperspirant active and other materials such as perfumes. The combined components are heated to about 100° C. with agitation to form a hot liquid, after which all other materials are added to the heated liquid. The heated liquid is allowed to cool with agitation until just before the point of solidification, at which point the cooled, liquid composition is filled into applicator packages and allowed to cool and solidify to the requisite product hardness.

Each of the exemplified compositions comprise a crystalline gel matrix containing crystalline particles having an aspect ratio of greater than about 6, and an average crystalline gellant particle size of less than about 1 μm. Each of the exemplified compositions also have a visible residue index of between about 11 and about 30 L-value, a product hardness of between about 500 and 5,000 gram·force, and a G'/G" ratio of between about 0.1 and about 100. Each of the exemplified antiperspirant compositions are applied topically to the axilla area of the skin, in accordance with the methods of use described herein, and provide improved low residue performance, efficacy and aesthetics.

| Component | Examples 1–6 | | | | | |
|---|---|---|---|---|---|---|
| | No. 1 | No. 2 | No. 3 | No. 4 | No. 5 | No. 6 |
| D5 Cyclomethicone[1] | 15 | 19.5 | 45 | 40 | 60 | 47.8 |
| 12-Hydroxystearic acid | 7.0 | 3.5 | 7.0 | 7.0 | 8.0 | 7 |
| 2-Dodecyl-N,N'-dibutylsuccinamide | 2 | 1 | 2 | 2 | — | — |
| Polyether siloxane[2] | — | — | — | — | 5.0 | — |
| Dimethicone copolyol[3] | 50 | 50 | — | — | — | — |
| Dimethyl-diphenyl-siloxane[4] | — | — | 20 | — | — | — |
| Silicone polyether copolymer[5] | — | — | — | 25 | — | — |
| Sucrose polyester[6] | — | — | — | — | 1.0 | — |
| Octodocecanol | — | — | — | — | — | 14 |
| Dimethicone copolyol[7] | — | — | — | — | — | 2 |
| Disodium EDTA | — | — | — | — | — | 0.2 |
| C20–C40 Alcohol[8] | — | — | — | — | — | 0.5 |
| C20–C40 Pareth 10[9] | — | — | — | — | — | 1.25 |
| C20–C40 Pareth 40[10] | — | — | — | — | — | 1.25 |
| Al Zr trichlorohydrex glyc | 26 | 26 | 26 | 26 | 26 | 26 |
| Residue (L-Value) | 23.5 | 24 | 23 | 21 | 29 | |
| Hardness (gram-Force) | 2300 | 1200 | 850 | 750 | 1230 | |
| G'\G" | 15 | 10 | 10 | 5 | 10 | |

[1]Dow Corning 245 Fluid; General Electric SF-1202
[2]EM-97 from Goldschmidt
[3]DC-3225C from Dow Corning
[4]SF-1023 from G.E. Silicones
[5]SF-1188a from G.E. Silicones
[6]Sucrose octaester esterified predominantly with behenic acid moieties
[7]DC-1401 from Dow Corning
[8]Unilin 425 from Petrolite
[9]Unithox 450 from Petrolite
[10]Unithox 480 from petrolite

What is claimed is:

1. An anhydrous antiperspirant gel-solid stick composition comprising:
   (a) from about 0.5% to about 60% by weight of particulate antiperspirant active;
   (b) from about 1% to about 15% by weight of a solid non-polymeric gellant that is substantially free of organic polymeric gellants, dibenzylidene alditol, inorganic thickening agents, derivatives of n-acyl amino acid, or combinations thereof;
   (c) from about 10% to about 80% by weight of an anhydrous liquid carrier containing a silicone liquid carrier selected from the group consisting of polyalkylsiloxanes, polyalkyarylsiloxanes, polyestersiloxanes, polyethersiloxane copolymers, polyfluorosiloxanes, polyaminosiloxanes, and combinations thereof; and
wherein the composition has a visible residue index of from about 11 to about 30 L-value, a product hardness of from about 500 gram·force to about 5,000 gram·force, and a ratio of an elastic to viscous moduli of from about 0.1 to about 100.

2. The composition of claim 1 wherein the composition contains from about 0.1% to about 50% by weight of the silicone carrier.

3. The composition of claim 2 wherein the composition contains from about 1% to about 10% by weight of the silicone carrier.

4. The composition of claim 2 wherein the silicone carrier is selected from the group consisting of dimethicone copolyol, tetraethoxysilane, tetramethoxysilane, hexamethoxysilicone, oxmethoxytrisiloxane, phenyl trimethicone, tetramethyl-tetraphenyl-trisiloxane; laurylmethicone copolyol cetyl dimethicone, stearyl dimethicone, caproyl trimethicone, stearoxytrimethylsilane dimethiconal, dimethiconol, stearoxytrimethylsilane, trimethylsilylamodimethicone, trimethylsilylamodimethicone, trimethylsiloxysilicate, dimethyl-diphenyl-siloxane, methylphenyl siloxane, methylphenyl siloxane, hexamethyl-3-phenyl-3-[[trimethylsilyl]oxy]trisiloxane, trimethylsiloxysilicate, stearoxy dimethicone, tetrabutoxypropyl trisiloxane, bisphenylhexamethicone tris[tributoxysiloxy]methylsilane, and combinations thereof.

5. The composition of claim 2 wherein the solid non-polymeric gellant is selected from the group consisting of 12-hydroxystearic acid, esters of 12-hydroxystearic acid, amides of 12-hydroxystearic acid, and combinations thereof.

6. The composition of claim 5 wherein the solid non-polymeric gellant is selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and combinations thereof.

7. The composition of claim 6 wherein the solid non-polymeric gellant is 12-hydroxystearic acid.

8. The composition of claim 2 wherein the solid non-polymeric gellent comprises a gellant conforming to the formula:

$$\begin{array}{c} R_9 \quad O \quad R_5 \\ | \quad \| \quad | \\ R_1-C'-C-N-R_2 \\ | \quad\quad\quad\quad R_7 \\ a | \quad\quad\quad\quad | \\ R_3-X-Y-Z-R_8 \\ | \\ O \\ \| \\ R_{11}-C"-C-N-R_4 \\ | \quad\quad | \\ R_{10} \quad R_6 \end{array}$$

wherein
a) $R_1$ is nil, hydroxy, hydrogen, aryl, siloxane or saturated or unsaturated, substituted or unsubstituted, straight, branched or cyclic chain $C_1-C_{22}$ alkyl, $C_1-C_{22}$ alkenyl, $C_1-C_{22}$ alkoxy, $C_1-C_{22}$ alkyl esters, $C_1-C_{22}$ alkyl ethers, or $C_1-C_{22}$ alkyl substituted aryl;

b) $R_2$, $R_4$, $R_5$ and $R_6$ are independently or together, hydrogen, hydroxy, aryl, siloxane or saturated or unsaturated, substituted or unsubstituted, straight, branched or cyclic chain $C_1-C_{22}$ alkyl, $C_1-C_{22}$ alkenyl, $C_1-C_{22}$ alkoxy, $C_1-C_{22}$ alkyl esters, $C_1-C_{22}$ alkyl ethers, or $C_1-C_{22}$ alkyl substituted aryl;

c) $R_3$ is nil, hydroxy, hydrogen, saturated or unsaturated, substituted or unsubstituted, straight, branched or cyclic chain $C_1$–$C_4$ alkyl, $C_1$–$C_4$ alkenyl, $C_1$–$C_4$ alkoxy, $C_1$–$C_4$ alkyl esters or $C_1$–$C_4$ alkyl ethers;

d) $R_7$ and $R_8$ are independently or together, nil, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl;

e) $R_9$ is nil or hydrogen;

f) $R_{10}$ and $R_{11}$ are independently or together, nil, hydrogen, hydroxy, aryl, siloxane or saturated or unsaturated, substituted or unsubstituted, straight, branched or cyclic chain $C_1$–$C_6$ alkyl, $C_1$–$C_6$ alkenyl, $C_1$–$C_6$ alkoxy, $C_1$–$C_6$ alkyl esters, $C_1$–$C_6$ alkyl ethers, or $C_1$–$C_6$ alkyl substituted aryl;

g) X is nil, nitrogen, aryl or –(CH$_2$)$_n$– where n is an integer from 1 to 6;

h) Y is nil, acyl or carbonyl;

i) Z is nil, hydrogen, hydroxy, aryl, siloxane, nitrogen or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl; and j) "a" is a double or single bond, provided:
   (i) when X is nil, Y, Z, $R_3$, $R_7$ and $R_8$ are nil, C' is bonded directly to C" and $R_1$ is not a hydrogen;
   (ii) when X and Z are not nil and Y is nil, X is directly bonded to Z;
   (iii) when Z is nil, a hydrogen or a hydroxy, $R_7$ and $R_8$ are nil; and
   (iv) when "a" is a double bond, $R_3$ and $R_9$ are nil.

9. The composition of claim 5 wherein the solid non-polymeric gellant are elongated crystalline particles having an aspect ratio of at least about 2.

10. The composition of claim 9 wherein the solid non-polymeric gellant are elongated crystalline particles having an aspect ratio of at least about 6.

11. The composition of claim 5 herein the solid non-polymeric gellant are crystalline particles having an average particle size of less than about 1 μm.

12. The composition of claim 11 wherein the composition has a Differential Scanning Calorimeter onset temperature of from about 25° C. to about 85° C.

13. The composition of claim 12 wherein the composition has a Differential Scanning Calorimeter onset temperature of from about 30° C. to about 60° C.

14. The composition of claim 11 wherein the solid non-polymeric gellant are crystalline particles having an average particle size of less than about 0.2 μm.

15. The composition of claim 5 wherein the composition has a product hardness of from about 750 gram·force to about 2,000 gram·force.

16. The composition of claim 15 wherein the composition has a ratio of an elastic to viscous moduli of from about 0.1 to about 50.

17. The composition of claim 5 wherein the composition further comprises a volatile silicone carrier liquid carrier which conforms to the formula:

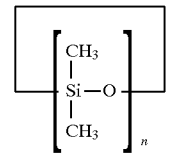

wherein n is from about 3 to about 7.

18. The composition of claim 17 wherein the anhydrous liquid carrier further comprises a non-volatile silicone liquid carrier having a viscosity of less than about 100,000 centistokes.

19. The composition of claim 5 wherein the composition is substantially free of solid fatty alcohols having from 12 to 40 carbon atoms.

20. The composition of claim 5 wherein the particulate antiperspirant active has an average particle size of from about 20 μm to about 100 μm.

21. The composition of claim 5 wherein the particulate antiperspirant active has an average particle size of less than about 2 μm.

22. A method for treating or reducing perspiration wetness and malodor, comprising applying from about 0.1 gram to about 20 grams of the composition of claim 1 to the desired area of the skin.

23. A method for treating or reducing perspiration wetness and malodor, comprising applying from about 0.1 gram to about 20 grams of the composition of claim 7 to the desired area of the skin.

24. A method for treating or reducing perspiration wetness and malodor, comprising applying from about 0.1 gram to about 20 grams of the composition of claim 11 to the desired area of the skin.

25. A method for treating or reducing perspiration wetness and malodor, comprising applying from about 0.1 gram to about 20 grams of the composition of claim 17 to the desired area of the skin.

* * * * *